(12) United States Patent
Majeed et al.

(10) Patent No.: US 10,864,242 B2
(45) Date of Patent: Dec. 15, 2020

(54) APHRODISIAC COMPOSITION AND MANAGEMENT OF MALE SEXUAL DYSFUNCTION

(71) Applicants: Muhammed Majeed, Bangalore (IN); Kalyanam Nagabhushanam, East Windsor, NJ (US); Sarang Bani, Bangalore (IN); Anjali Pandey, Bangalore (IN)

(72) Inventors: Muhammed Majeed, Bangalore (IN); Kalyanam Nagabhushanam, East Windsor, NJ (US); Sarang Bani, Bangalore (IN); Anjali Pandey, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 78 days.

(21) Appl. No.: 16/386,376

(22) Filed: Apr. 17, 2019

(65) Prior Publication Data
US 2020/0268822 A1   Aug. 27, 2020

(30) Foreign Application Priority Data
Feb. 22, 2019   (IN) .............................. 201941006993

(51) Int. Cl.
*A61K 36/81*   (2006.01)
*A61K 36/48*   (2006.01)
*A61P 15/10*   (2006.01)
*A61K 36/906*   (2006.01)
*A61K 36/67*   (2006.01)
*A61K 36/53*   (2006.01)

(52) U.S. Cl.
CPC .............. *A61K 36/81* (2013.01); *A61K 36/48* (2013.01); *A61K 36/53* (2013.01); *A61K 36/67* (2013.01); *A61K 36/906* (2013.01); *A61P 15/10* (2018.01)

(58) Field of Classification Search
None
See application file for complete search history.

(56) References Cited

U.S. PATENT DOCUMENTS

2011/0064712 A1 *   3/2011   Amato ............... A61K 31/7076
424/94.2

FOREIGN PATENT DOCUMENTS

WO   WO-2017153555 A1 *   9/2017   ........... A61K 9/2013
WO   WO-2018033892 A1 *   2/2018   ........... A61K 36/736

* cited by examiner

*Primary Examiner* — Russell G Fiebig

(57) ABSTRACT

The present invention discloses a composition for the therapeutic management of male sexual dysfunction and related disorders. Specifically, the invention discloses a composition comprising 60-65% w/w *Withania somnifera* extract, 12-18% w/w *Mucana pruriens* extract, 5-10% w/w *Coleus forskolii* extract, 12-18% w/w *Kaempferia parviflora* extract, 0.1-2% w/w *Piper nigrum* extract, for use as an aphrodisiac.

7 Claims, 4 Drawing Sheets

APHRODISIAC COMPOSITION AND MANAGEMENT OF MALE SEXUAL DYSFUNCTION

CROSS REFERENCE TO RELATED APPLICATIONS

This is a conventional application claiming priority from Indian patent application number IN201941006993 filed on Feb. 22, 2019.

FIELD OF INVENTION

The present invention pertains to compositions for the therapeutic management of male sexual dysfunction and associated disorders. Specifically, the invention relates to compositions comprising plant extracts and phytochemical for the management of disorders related to male sexual dysfunction.

BACKGROUND OF THE INVENTION

Male sexual arousal is triggered by complex biochemical pathways, physical and psychological events that involve the nervous and vascular systems which include the brain, neurotransmitters, secondary messengers, smooth muscles, blood vessels etc. Sexual dysfunction occurs if the pathways involving any of the above are disturbed. The common types of male sexual dysfunction include erectile dysfunction, premature ejaculation, delayed or inhibited ejaculation, and reduced libido.

A combination of physical and physiological issues can cause sexual dysfunction in males, particularly erectile dysfunction. The brain plays a key role in triggering the series of physical events that cause an erection, starting with feeling of sexual excitement. Depression, anxiety or other mental health conditions, stress or relationship problems due to stress, poor communication causes or worsens erectile dysfunction.

State of the art explains penile erection is a complex process involving psychogenic and hormonal functionality and a neurovascular non adrenergic, non cholinergic mechanism. Nitrous oxide, produced by Corpora cavernosa is the main vasoactive noncholinergic and non adrenergic neurotransmitter and chemical mediator of erectile function. Nitric oxide stimulates the enzyme guanylate cyclase that converts GTP to 3', 5'-cyclic guanosine monophosphate (cGMP). cGMP causes smooth muscles in the arteries to relax which increases the blood flow to the penis. The veins that carry blood away from the penis constrict, thus trapping the pressurized blood in the Corpora cavernosa resulting in the erection.

Moreover, the cGMP level plays major role in maintaining the erection for longer time. Ideally the cGMP is converted into 5' GMP by phospho diesterase enzyme, thus reducing the erection. Inhibition of Phospho diesterase enzyme can prolong the erection of the penis providing sexual satisfaction (Please provide reference)

Hence for treatment of penile dysfunction and therapeutic management of associated male sexual dysfunctions it is necessary to target every stage of mechanism wherein level of nitric oxide are increased increasing the penile blood flow, activation of enzyme guanylate cyclase to increase the levels of cyclic monophosphate (cGMP), and increased levels of cGP specific protein kinase to increase smooth muscle relaxation.

State of the art chemical compositions includes one or more agents that act through various routes in treatment of male sexual dysfunction. Few prior arts are mentioned below:

Wipo application number WO2018220232 explains composition comprising botulinum toxin mainly onabotulinum toxin A, abobotulinumtoxin A and incobotulinumtoxin A; PDE5 inhibitors mainly sildenafil citrate, lodenafil, avanafil, mirodenafil, sildeafil, tadalafil and other derivatives for simultaneous, sequential or separate use in the treatment of erectile functions.

U.S. application Ser. No. 15/434,226 titled Composition and method for treatment of erectile dysfunction disclosed use of one chemically active anti erectile dysfunction drug (AED) like vaedenafil, avanafil and its acceptable salts along with cannabis and its extract in combination.

U.S. Pat. No. 7,147,874 discloses pharmaceutical composition for the prevention and treatment of premature ejaculation and/or hypersensitivity of sexual stimulation are provided. The composition contains purified sumsoo extract and purified ginseng extract containing saponin as the main component, without other herbal essential oil components.

US 2006/0269623 teaches about herbal compositions and methods of treatment for prevention or treatment of erectile dysfunction disorders and ameliorating symptoms thereof and as a preventative measure against erectile dysfunction. The methods comprise administering a therapeutically effective composition of matter comprising the following herbal and other components: *Herba cynomorii, Rhizhomnas atractylodis macrocephalae, Radix rehmannia glutinosea longui, Herba epimedii, Fructus lycii, Fructus schisandrae chinensis, Radix poloygoni multiflor, Cortex cinnamonia cassiae, Fructus amoni*, and *Radix ginseng*. Kotta et al., (Kotta et al., Exploring scientifically proven herbal aphrodisiacs, Pharmacogn Rev. 2013 January-June; 7(13): 1-10) reviews about the different herbal aphrodisiacs used in the Ayurvedic system of medicine.

Various other devices such as vacuum devices, penile implants are available, but benefit only those patients whose function has been severely impaired. It has been observed that bruising, skin breakdown, and penile pain may occur while using these devices.

The existing treatments for male sexual dysfunction do not target all the aspects of sexual dysfunction leading to relapse of the condition. Moreover they are reported to have side effects or are not very comfortable for usage. Hence, there is an unmet industrial need to provide a product which is safe and efficient in therapeutic management of male sexual dysfunction by targeting the complete pathophysiological aspects of Sexual Dysfunction.

The present invention solves the above problem by disclosing a composition comprising plant extracts and phytochemical for use as an aphrodisiac and in the therapeutic management of male sexual dysfunction and related disorders.

It is the principle object of the invention to disclose a composition comprising 60-65% w/w *Withania somnifera* extract standardized to contain 0.25% withaferin and 7% withanolides, 12-18% w/w *Mucana pruriens* extract standardized to contain 10% w/w L-dopa, 5-10% w/w *Coleus forskohlii* extract standardized to contain 10% w/w forskolin. 12-18% w/w *Kaempferia parviflora* standardized to contain 2.5% w/w of 5,7-dimethoxyflavone and not less than 10% w/w Total fand 0.1-2% w/w *Piper nigrum* extract standardized to contain 95% w/w Piperine for use as an aphrodisiac.

It is another object of the invention to disclose a method for the therapeutic management of male sexual dysfunction and related disorders using a composition comprising 60-65% w/w *Withania somnifera* extract standardized to contain 0.25% withaferin and 7% withanolides, 12-18% w/w *Mucana pruriens* extract standardized to contain 10% w/w L-dopa, 5-10% w/w *Coleus forskohlii* extract standardized to contain 10% w/w forskolin, 12-18% w/w *Kaempferia parviflora* standardized to contain 2.5% w/w of 5,7-dimethoxyflavone and not less than 10% w/w Total flavonoids and 0.1-2% w/w *Piper nigrum* extract standardized to contain 95% w/w Piperine.

The present invention solves the above objectives and provides further related advantages.

SUMMARY OF THE INVENTION

The present invention provides a composition for the therapeutic management of male sexual dysfunction and related disorders.

More specifically, the invention discloses a composition comprising 60-65% w/w *Withania somnifera* extract standardized to contain 0.25% withaferin and 7% withanolides, 12-18% w/w *Mucana pruriens* extract standardized to contain 10% w/w L-dopa, 5-10% w/w *Coleus forskolii* extract standardized to contain 10% w/w forskolin, 12-18% w/w *Kaempferia parviflora* standardized to contain 2.5% w/w of 5,7-dimethoxyflavone and not less than 10% w/w Total flavonoids and 0.1-2% w/w *Piper nigrum* extract standardized to contain 95% w/w Piperine for use as an aphrodisiac by increasing the levels of nitric oxide, testosterone and cGMP.

Other features and advantages of the present invention will become apparent from the following more detailed description, taken in conjunction with the accompanying images, which illustrate, by way of example, the principle of the invention.

DESCRIPTION OF PREFERRED EMBODIMENTS

Figure 1:
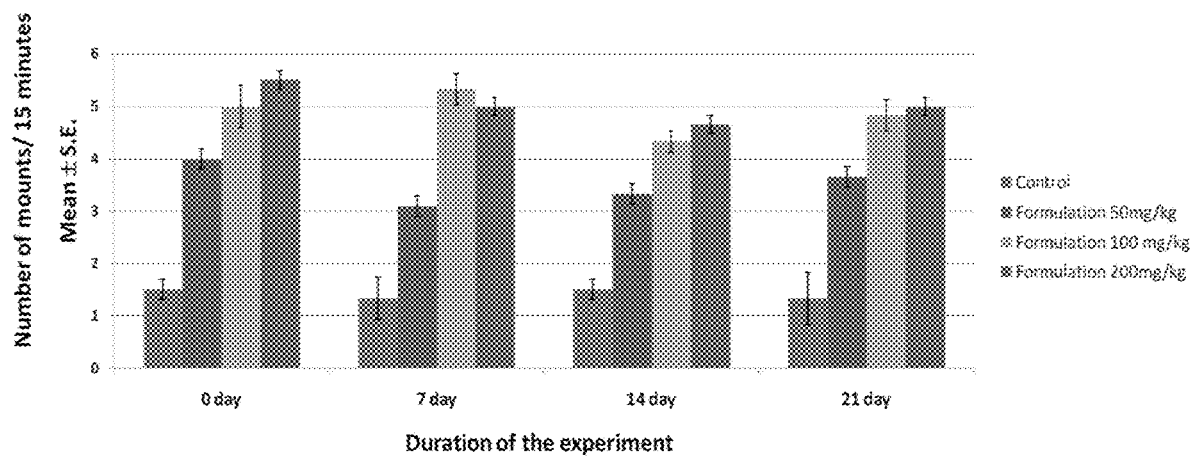
FIG. 1 is a graphical representation showing the effect of the formulation on mounting behavior in male wistar rats (long term effect).

The invention is described in detail with each preferred embodiment for better understanding and to enable a person moderately skilled in the art to manifest or practice the invention.

In the most preferred embodiment the present invention discloses a composition comprising 60-65% w/w *Withania somnifera* extract, 12-18% w/w *Mucana pruriens* extract, 5-10% w/w *Coleus forskohlii* extract, 12-18% w/w *Kaempferia parviflora* extract and 0.1-2% w/w *Piper nigrum* extract. In a related aspect, the composition comprises at least one phytochemical selected from the group of phospho diesterase 5 (PDE-5) inhibitor; testosterone enhancer, Nitric oxide enhancer, cGMP enhancer, anti-spasmodic and vasodilator, androgen receptor activator and cGMP protein kinase activator.

In a related aspect, the *Withania somnifera* extract is standardized to contain 0.25% withaferin and 7% withanolides. In another related aspect, the *Mucana pruriens* extract is standardized to contain 10% w/w L-dopa. In yet another related aspect, the *Coleus forskohlii* extract is standardized to contain 10% w/w forskolin. In another related aspect, the *Kaempferia parviflora* extract is standardized to contain 2.5% w/w of 5,7-dimethoxyflavone and not less than 10% w/w Total flavonoids.

In another preferred embodiment, the invention discloses a composition comprising 60-65% w/w *Withania somnifera* extract standardized to contain 0.25% withaferin and 7% withanolides, 12-18% w/w *Mucana pruriens* extract standardized to contain 10% w/w L-dopa, 5-10% w/w *Coleus forskohlii* extract standardized to contain 10% w/w forskolin, 12-18% w/w *Kaempferia parviflora* standardized to contain 2.5% w/w of 5,7-dimethoxyflavone and not less than 10% w/w Total flavonoids and 0.1-2% w/w *Piper nigrum* extract standardized to contain 95% w/w Piperine for use as an aphrodisiac.

In a related aspect, the composition comprises at least one phytochemical selected from the group of phospho diesterase 5 (PDE-5) inhibitor; testosterone enhancer, Nitric oxide enhancer, cGMP enhancer, anti-spasmodic and vasodilator, androgen receptor activator and cGMP protein kinase activator. In another related aspect, the composition is formulated with pharmaceutically/nutraceutically acceptable excipients, adjuvant, diluents or carriers and administered in the form of tablets, capsules, syrups, gummies, powders, suspensions, emulsions, chewable, candies or eatables.

In another preferred embodiment, the invention discloses a method for increasing libido in mammals, said method comprising step of administering an effective dose of a composition, based on the body weight of the mammal, comprising 60-65% w/w *Withania somnifera* extract standardized to contain 0.25% withaferin and 7% withanolides, 12-18% w/w *Mucana pruriens* extract standardized to contain 10% w/w L-dopa, 5-10% w/w *Coleus forskohlii* extract standardized to contain 10% w/w forskolin, 12-18% w/w *Kaempferia parviflora* standardized to contain 2.5% w/w of 5,7-dimethoxyflavone and not less than 10% w/w Total flavonoids and 0.1-2% w/w *Piper nigrum* extract standardized to contain 95% w/w Piperine to mammals in need of such effect. In a related aspect, the composition comprises at least one phytochemical selected from the group of phospho diesterase 5 (PDE-5) inhibitor; testosterone enhancer, Nitric oxide enhancer, cGMP enhancer, anti-spasmodic and vasodilator, androgen receptor activator and cGMP protein kinase activator. In a related aspect, the effect dose of the composition is 50-200 mg/kg body weight. In another related aspect, the mammal is preferably male. In another related aspect, the mammal is preferably human. In another related aspect, the composition is formulated with pharmaceutically/nutraceutically acceptable excipients, adjuvant, diluents or carriers and administered in the form of tablets, capsules, syrups, gummies, powders, suspensions, emulsions, chewable, candies or eatables.

In yet another preferred embodiment, the invention discloses a method for therapeutic management of male sexual dysfunction and related disorders in mammals, said method comprising step of administering an effective dose of a composition, based on the body weight of the mammal, comprising 60-65% w/w *Withania somnifera* extract standardized to contain 0.25% withaferin and 7% withanolides, 12-18% w/w *Mucana pruriens* extract standardized to contain 10% w/w L-dopa, 5-10% w/w *Coleus forskohlii* extract standardized to contain 10% w/w forskolin, 12-18% w/w *Kaempferia parviflora* standardized to contain 2.5% w/w of 5,7-dimethoxyflavone and not less than 10% w/w Total flavonoids and 0.1-2% w/w *Piper nigrum* extract standardized to contain 95% w/w Piperine to mammals in need of such effect. In a related aspect, the male sexual dysfunction is selected from the group comprising erectile dysfunction, premature ejaculation, Delayed or inhibited ejaculation, and reduced libido. In a related embodiment, the male sexual dysfunction is preferably erectile dysfunction and reduced libido. In a related aspect, the management of male sexual dysfunction is brought about by inhibiting phospho diesterase 5 (PDE-5), enhancing testosterone, Nitric oxide and cGMP levels and activating androgen receptor and cGMP protein kinase. In a related aspect, the effect dose of the composition is 50-200 mg/kg body weight. In another related aspect, the mammal is preferably male. In another related aspect, the mammal is preferably human. In another related aspect, the composition is formulated with pharmaceutically/nutraceutically acceptable excipients, adjuvant, diluents or carriers and administered in the form of tablets, capsules, syrups, gummies, powders, suspensions, emulsions, chewable, candies or eatables.

Specific illustrative examples enunciating the most preferred embodiments are included herein below.

EXAMPLES

Example 1: Details of the Composition

The present invention discloses a synergistic composition comprising 60-65% w/w *Withania somnifera* extract, 12-18% w/w *Mucana pruriens* extract, 5-10% w/w *Coleus forskohlii* extract, 12-18% w/w *Kaempferia parviflora* extract and 0.1-2% w/w *Piper nigrum* extract. The details and the intended therapeutic potential in the management of male sexual dysfunction of the individual plant extracts are provided below:

*Withania somnifera* commonly known as ashwagandha, Indian *ginseng*, poison gooseberry or winter cherry is a plant in the Solanacea family. Synonyms for *Withania somnifera* are *Physalis somnifera* L., *Withania kansuensis* Kuang & A. M. Lu and *Withania microphysalis*. The main phytochemical component constitutes withanolides which are triterpene lactones mainly withanolides, withaferin A, alkaloids, steroidal lactones, tropine and cuscohygrine. (Ashwagandha". Drugs.com. 2009. Retrieved 27 Dec. 2018). The alkaloids of *Withania somnifera* are reported to increase production of nitric oxide and improve vascular endothelial abnormalities. The sterols present in the extract stimulate sexual and adrenal functions (Kumar et. al., Chemistry and pharmacology of *Withania somnifera*: An update, TANG Humanitas Medicine, 2015; 5(1):1-13) and flavonoids aids in the protections of cardiovascular system. (Narinderpal et. al., A Review on Pharmacological Profile of *Withania somnifera* (Ashwagandha), Research & Reviews: Journal of Botanical Sciences, 2013; 2(4); 1-9)

*Mucana pruriens* commonly known as velvet bean, Bengal velvet bean, Florida velvet bean, Mauritius velvet bean, yokohama velvet bean, cowage co witch, lacuna bean and Lyon bean. It is a tropical legume native to Africa and tropical Asia and widely naturalizes and cultivated. The seeds of the plant contain L-Dopa, with trace amount of serotonin, nicotine and bufotenine. The plant and its extracts have been long used in tribal communities as a toxin antagonist for various snakebites. It has also been used in traditional ayurveda Indian medicine to treat diseases including Parkinson's disease (Cilia et. al., *Mucana Pruriens* in Parkinson disease, Neurology, 2017 Aug. 1; 89(5): 432-438). Levodopa or L-dopa present in the seed of the plant is vital for the synthesis of dopamine, a neurotransmitter that plays a important function in sexual arousal. L-dopa helps to prolong time of intercourse and is reported to address the symptoms of premature ejaculation. (Morales et. al. Evolving therapeutic strategies for premature ejaculation: The search for on-demand treatment—topical versus systemic, Canadian Urological Association Journal, 2012; 6(5) 380-385)

*Piper nigrum* is a flowering vine in the family Piperaceae, cultivated for its fruit, which is usually dried and used as a spice and seasoning agent, the fruit contains many terpenes, including germacrene, limoline, pipene and alpha-phellandrene and beta-caryophyllene. (Pund et. al. Nanoarchitectures for Neglected Tropical Protozoal Diseases: Challenges and State of the Art, Science Direct, 2016) Black pepper is also reported to contain Piperine which is used as a bioavailability enhancer. (Kesarwani et. al. Bioavailability enhancers of herbal origin: An overview, Asia Pacafic Journal of Topical Biomedicine, 2013; 3(4) 253-266). Piperine is also reported to increase the levels of CoQ10 in the blood which triggers blood flow to the entire body including penile vein.

*Coleus forskohlii* also known as *Plectranthus barbatus* is a tropical perennial plant related to the typical *coleus* species. It produces forskolin, an extract useful for pharmaceutical preparations. In ayurveda, *Coleus* is used to treat heart disease, spasmodic pain, painful urination and convulsions (Meghwal et. al. Nutritional Constituent of Black pepper as Medicinal Modules: A Review. Open Access Scientific Reports, 2012, 1(1) 1-7). Forskolin is reported to increase cAMP, androgen receptor activity and promote steroidogensis. Forskolin also increases androgen receptor sensitivity thereby increasing the utilization of testosterone (Neto et. al. Vasodilation induced by forskolin involves cyclic GMP production. Journal of Biophysical Chemistry, 2011 2(4), 1-7)

*Kaempferia parviflora* also known as Thai black ginger, Thai ginseng or krachai dum, is an herbaceous plant in the family Zingiberaceae. *K. parviflora* has pharmacological activities such as anti-inflammatory, antioxidant, and aphrodisiac, anti gastric ulcer effect, antiplasmodial, antifungal, and antibacterial activities. *K. parviflora* is reported to contain many flavonoids which is responsible for its therapeutic potential. The plant is known for its PDE5 inhibition and activation of cGMP protein kinase which in turn decrease the concentration of Ca+ and accelerates smooth muscles relaxation in the penile smooth muscles (Chen et. al. *Kaempferia parviflora* and its methoxyflavone: Chemistry and Biological Activities. Evidence-Based Complementary and Alternative Medicine; 2018; Article ID 4057456, 1-15)

The composition disclosed in the invention targets all the mechanisms of male fertility and provides synergistic effects. The constituent of the composition is mentioned in table 1.

TABLE 1

Composition details

| Extract | Dose (mg/kg body weight) |
|---|---|
| *Withania somnifera* | 400 |
| *Mucana pruriens* | 100 |
| *Coleus forskohlii* | 50 |
| *Kaempferia parviflora* | 100 |
| *Piper nigrum* | 5 |

Example 2: Reproductive Performance Study

The invention composition was experimented in male wistar rats and observed for the reproductive performance studies. Both behavioral and biochemical assessments were carried out and the findings that support the claimed invention is described with examples in the detailed description of the invention.

Behavioral Assessment
Mounting Behavior:

TABLE 2

Effect of Formulation on mounting behavior in male wistar rats (Long term effect)

| Treatment | Dose (mg/kg) | No. of mounts per 15 minutes Mean ± SE | | | | Average increase (%) |
|---|---|---|---|---|---|---|
| | | 0 | 7 | 14 | 21 | |
| Control | — | 1.50 ± 0.22 | 1.33 ± 0.21 | 1.33 ± 0.21 | 1.50 ± 0.22 | |
| Formulation | 50 | 4.00 ± 0.25 (167) | 3.16 ± 0.30 (138) | 3.33 ± 0.2 (150) | 3.66 ± 0.21 (144) | 149.75 |
| Formulation | 100 | 5.00 ± 0.25 (233.3) | 5.33 ± 0.60 (300) | 4.33 ± 0.21 (225) | 4.83 ± 0.40 (222) | 245.07 |
| Formulation | 200 | 5.50 ± 0.34 (267) | 5.00 ± 0.60 (275.9) | 4.66 ± 0.21 (250.3) | 5.00 ± 0.25 (233) | 256.5 |

Non-estrous female rats were paired with males treated with single dose of the formulation. Animals were observed for 3 h (acute effect) for their sexual behavior (Tajuddin et. al., Aphrodisiac activity of 50% ethanol extracts of *Myristica fragrans* Houtt. (Nutmeg) and *Syzygium aromaticum* (L.) Merr. & Perry. (Clove) in male mice: a comparative study. BMC Complement Altern Med. 2003; 3:6.). Number of mounts along with other courtship activities recorded during 15 min observation period at the start of 1st hour. Female separated for 105 minutes. Again introduced and number of mounts observed for 15 minutes (3rd h). The results are tabulated in Table 2 and FIG. 1.

Values in parenthesis show percentage increase against control

The formulation significantly increased the number of mounts indicating that it is a very effective aphrodisiac.

Assessment of Mating:

After 1 hour of drug administration to a single male, five estrus females admitted into cage and kept as such overnight. Vaginal smear of each female rat examined microscopically for the presence of sperms the next morning. The stage of the estrous cycle was determined according to the criteria laid down by Dewsbury D A et. al., Effect of reserpine on the copulatory behaviour of Male rats. Physiol Behav. 1970; 5:1331-1333; Szechtman H, Moshe H, et. al. Sexual behaviour Pain sensitivity and stimulates endogenous opioid in male rats. Eur J Pharmacol. 1981; 70:279-285. The results are tabulated as table 3

TABLE 3

Effect of Formulation on mating performance in male wistar rats

| Treatment | Dose (mg/kg) | Number of pregnant females (5 females with a single male overnight) mean ± S.E. |
|---|---|---|
| Control | — | 1.33 ± 0.33 |
| Formulation | 50 | 2.16 ± 0.16 (62) |
| Formulation | 100 | 2.50 ± 0.33 (88) |
| Formulation | 200 | 2.66 ± 0.33 (100) |

Values in parenthesis show percentage increase against control

The results indicated an increase in mating performance of male rats administered with the formulation.

Observation of Coolidge Effect of Formulation in Male Wistar Rat

The Coolidge effect is a phenomenon wherein males exhibit renewed sexual interest when a new female is introduced, even after cessation of sex with prior but still available sexual partners. The effect in male wistar rats was determined by the procedures laid down by Reber, A. S. & Reber, E., The Penguin dictionary of psychology (3rd ed.), London: Penguin; Brown, R. E. (1974), "Sexual arousal, the Coolidge effect and dominance in the rat (*Rattus norvegicus*)", Animal Behaviour, 22 (3): 634-637; Lester, G L; Gorzalka, B B (1988), "Effect of novel and familiar mating partners on the duration of sexual receptivity in the female hamster", Behavioral Neural Biology, 49 (3): 398-405; Pinel, John (2007), Biopsychology (6th ed.), Boston: Pearson Allyn and BaconAfter 6 hours of drug treatment all the females were replaced with the fresh estrous female for next 6 hours.

Vaginal smears of all the females observed microscopically to confirm intromission and ejaculation in the first set and also in the second set of females to confirm the Coolidge effect. Table 4 indicates the percentage increase in no. of female pregnant rates against control samples and between first set of females and the replaced set.

TABLE 4

Coolidge effect of Formulation in male wistar rats

| Treatment | Dose (mg/g) | 1st 6 hr (mean ± S.E.) | 2nd 6 hr (mean ± S.E.) |
|---|---|---|---|
| Control | — | 1.66 ± 0.33 | 1.0 ± 0.22 |
| Formulation | 50 | 2.16 ± 0.30 (30.12) | 1.33 ± 0.49 (33) |
| Formulation | 100 | 2.50 ± 0.22 (50.60) | 1.45 ± 0.16 (45) |
| Formulation | 200 | 2.83 ± 0.54 (70.48) | 1.66 ± 0.42 (66) |

Values in parenthesis show percentage increase against control

Electric Barrier Effect on Sexual Behavior

The experimental procedures to observe electric barrier effect on sexual behavior were carried out as set forth by Graham J H et. al., Inhibitory avoidance behavior and memory assessment 2001. In Buccafusco J J (ed.), methods of Behavior analysis in Neuroscience, p. 141-151. Boca Raton: CRC Press. In this experiment the receptive (oestrous) female was kept on one side of the cage and test sample treated male rat on the other side of the same cage. In between was an electric barrier. Foot-shocks were delivered through grids present in the floor. Observations were recorded for both treated as well as the control groups with respect to the inclination of male rat to cross the barrier. The results are tabulated as table 5

TABLE 5

Effect of Formulation on electric barrier function

| Treatment | Dose (mg/kg) | Number of males that crossed the electric barrier/Total number of treated male rats |
|---|---|---|
| Control | — | 0/6 |
| Formulation | 50 | 1/6 |
| Formulation | 100 | 3/6 |
| Formulation | 200 | 3/6 |

Biochemical Assessment

Estimation of Testosterone

Testosterone is the principal male hormone produced by the interstitial (Leydig) cells of the male testes and in smaller amounts by the adrenals. Testosterone in males is responsible for maintenance of reproductive system and secondary sexual characters throughout the life of the male. The treated groups were given the formulation and levels were measured after 1 hr and 3 hr as per standard protocol.

Figure 2:
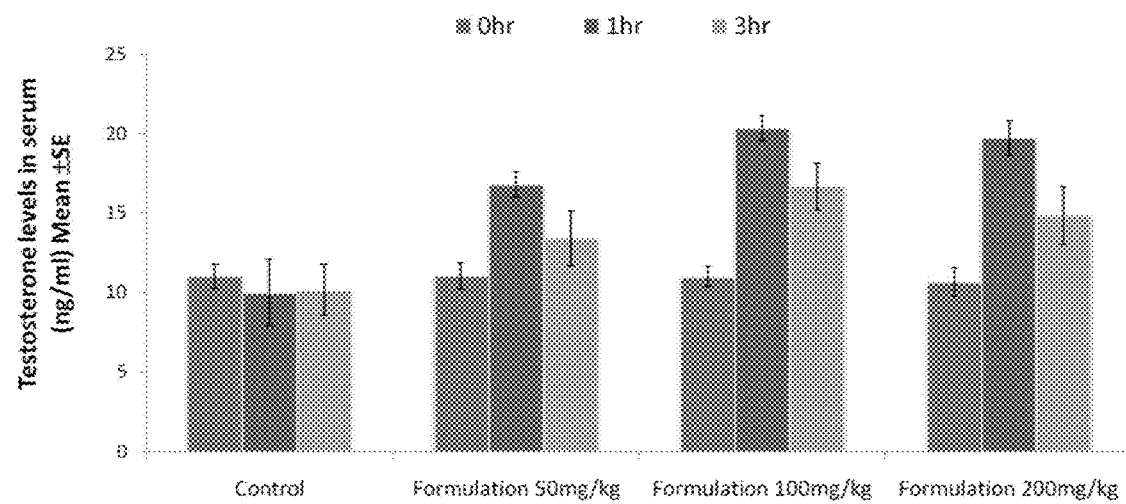
FIG. 2 is a graphical representation of serum testosterone levels in male wistar rats administered with different concentrations of the formulation.

The data shows increase in testosterone concentration in serum of treated animals after 1 hr and 3 hr (FIG. 2). Table 6 shows the Percentage activity of testosterone against control over a period of 21 days.

TABLE 6

Percentage activity of testosterone against control (Day 1-Day 21)

| Treatment | Dose (mg/kg) | Percentage increase of testosterone after 1 hr of administration of the formulation | | | |
|---|---|---|---|---|---|
| | | 1st day | 7th day | 14th day | 21st day |
| Control | — | — | — | — | — |
| Formulation | 50 | 11.49 | 14.58 | 17.47 | 23.96 |
| Formulation | 100 | 14.60 | 18.75 | 19.05 | 24.17 |
| Formulation | 200 | 12.30 | 19.16 | 20.46 | 20.83 |

The experimental animals had the same increase of testosterone throughout the use of formulation; it is a safe long-term solution for improved testosterone.

Androstenedione Estimation:

Androstenedione is a steroid hormone that mainly acts as a stepping stone in the manufacture of testosterone and estrogen within the body. Males with too little androstenedione may fail to develop the sexual characteristics associated with puberty, including pubic and body hair, growth of the sexual organs and deepening of the voice. Androstenedione was estimated as per standard protocol.

Figure 3:
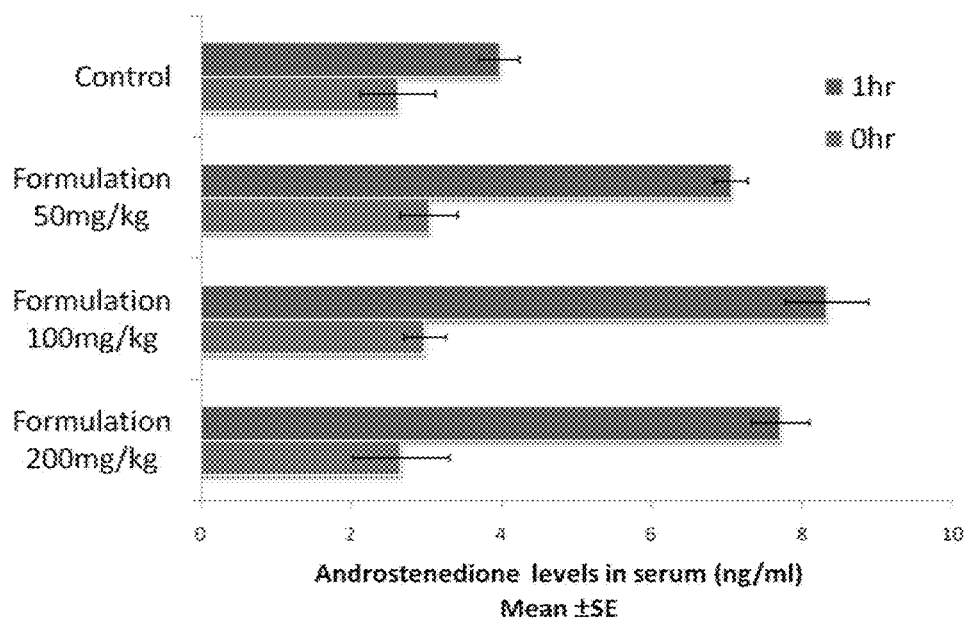
FIG. 3 is a graphical representation showing the serum androstenedione levels in male wistar rats administered with different concentrations of the formulation.

The results indicated an increase in androstenedione concentration in serum of treated animals after 1 hr of administration of the formulation (FIG. 3). Table 7 shows the Percentage activity of androstenedione against control over a period of 21 days.

TABLE 7

Percentage activity of androstenedione against control (Day 1-Day 21)

| Treatment | Dose (mg/kg) | Percentage increase of testosterone after 1 hr of administration of the formulation | | | |
|---|---|---|---|---|---|
| | | 1st day | 7th day | 14th day | 21st day |
| Control | — | — | — | — | — |
| Formulation | 50 | 33.10 | 14.01 | 19.19 | 22.21 |
| Formulation | 100 | 24.94 | 21.01 | 25.19 | 21.77 |
| Formulation | 200 | 24.48 | 23.54 | 27.13 | 28.14 |

Nitric Oxide Estimation:

The signal nitric oxide NO is released from nerve endings or from endothelial cells and activates a cascade reaction, which ultimately leads to an increased cellular concentration of cGMP (cyclic guanosine monophosphate). This second messenger molecule induces a series of events that lead to smooth-muscle relaxation through a reduction in the intracellular calcium ion concentration. The clinically important inhibitors (sildenafil, vardenafil and tadalafil) all act to promote smooth-muscle relaxation by their ability to allow cGMP to accumulate when nitric oxide is released, as is the case when sexual stimulation is present.

Nitric oxide was estimated in the serum of male wistar rats by ELISA. The method employed is as per the procedure described by Miles et. al. Determination of nitric oxide using fluorescence spectroscopy. Methods Enzymol. 1996; 268: 105-20. The results indicated an increase in Nitric oxide concentration in serum of treated animals after 1 hr of administration of the formulation (Table 8).

TABLE 8

Nitric oxide estimation in serum of male wistar rats by ELISA

| Treatment | Dose (mg/kg) | Nitric oxide (µmole/l) Mean ± S.E. |
|---|---|---|
| Control | — | 140.53 ± 4.25 |
| Formulation | 50 | 147.12 ± 8.16 (4.68) |
| Formulation | 100 | 159.47 ± 7.33 (13.48) |
| Formulation | 200 | 165.33 ± 12.33 (17.64) |

Figure 4:
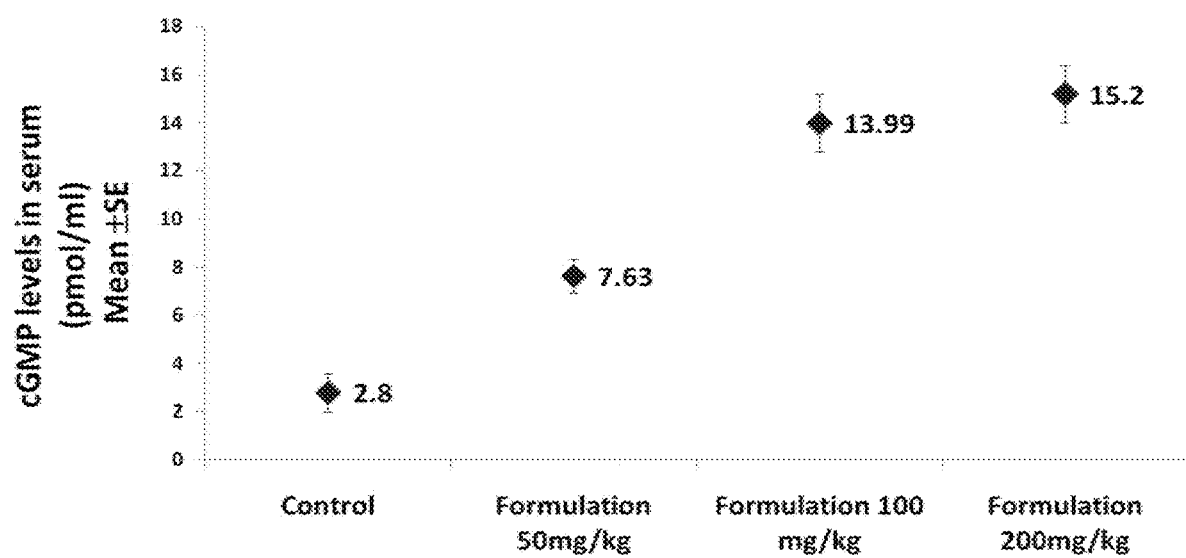
FIG. 4 is a graphical representation showing the levels of serum cGMP in male wistar rats administered with different concentrations of the formulation.
Figure 5:
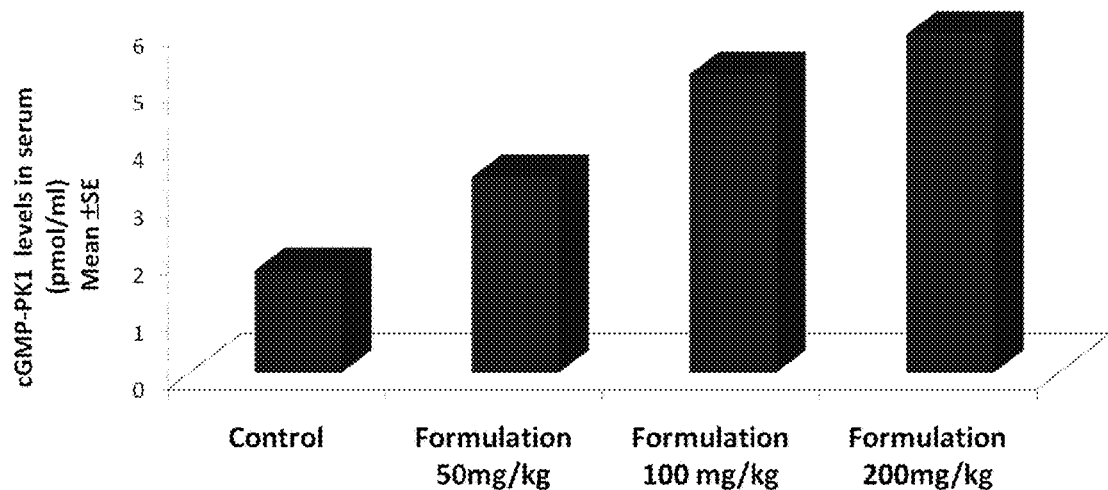
FIG. 5 is a graphical representation showing the levels of serum cGMP specific kinase in male wistar rats administered with different concentrations of the formulation.
Figure 6:
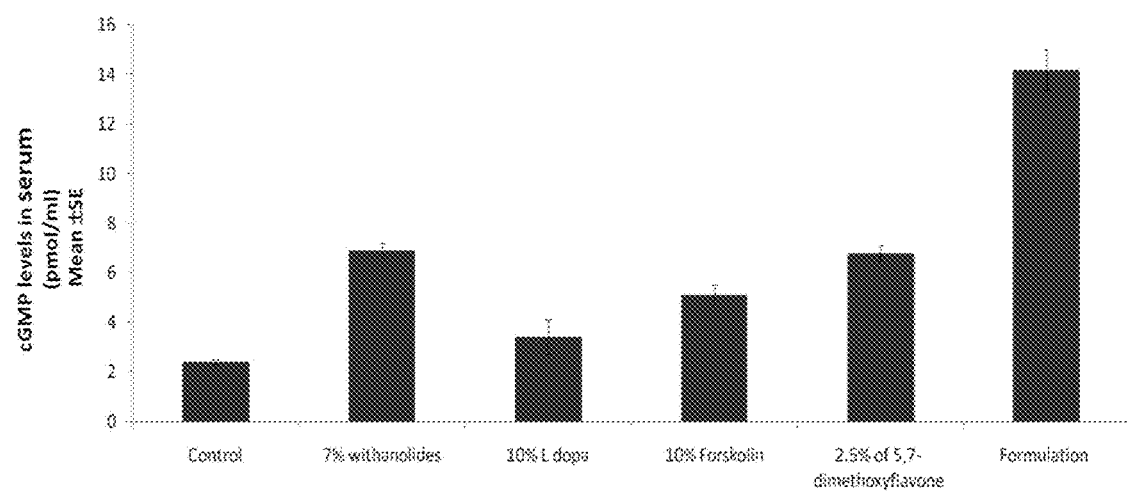
FIG. 6 is a graphical representation showing the comparative evaluation of the effect of formulation and individual plant actives on the levels of serum cGMP in male wistar rats
Figure 7:
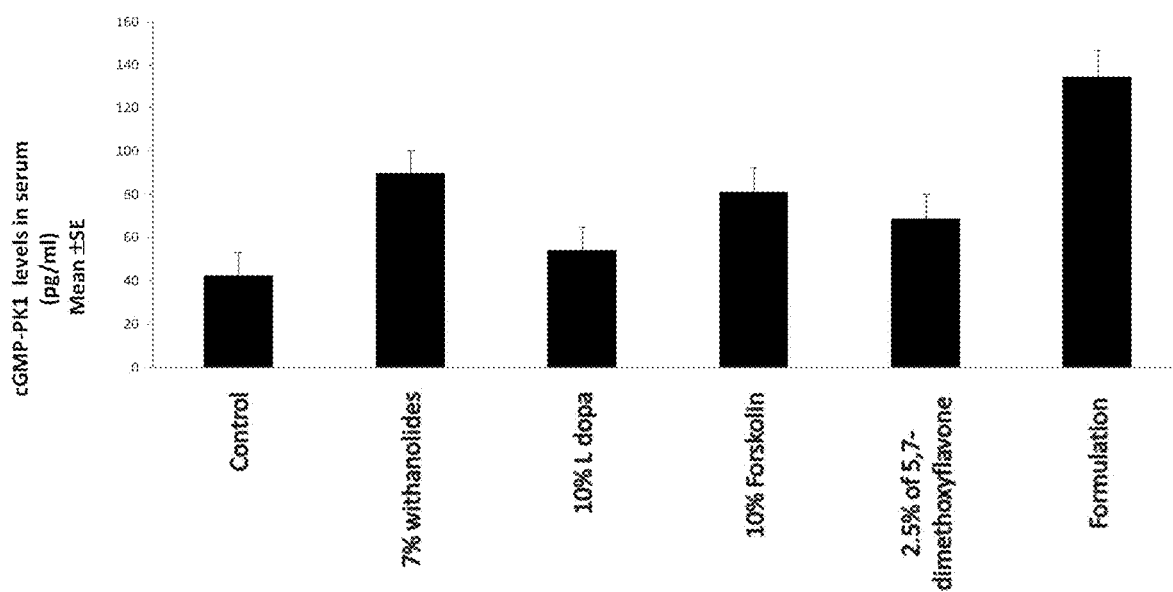
FIG. 7 is a graphical representation showing the comparative evaluation of the effect of formulation and individual plant actives on the levels of serum cGMP specific kinase in male wistar rats.

Values in parenthesis show percentage increase against control cGMP and cGMP Specific Protein Kinase Estimation The cGMP and cGMP specific protein kinase levels were also estimated in the serum of male wistar rats. The results indicated an increase in cGMP (FIG. 4) and cGMP-PK1 concentration (FIG. 5) in serum of treated animals after 1 hr of administration of the formulation The comparative effect of Individual ingredients and Formulation on cGMP and cGMP specific protein kinase were evaluated. The results indicated a synergistic effect in cGMP concentration (FIG. 6) and cGMP-PK1 concentration (FIG. 7) in serum of treated animals after 1 hr of administration of the test drugs when compared to the expression of cGMP in individual ingredient treated group.

Example 3: Cardiovascular Function Study

The objective of this study in rats was to determine the effect of the test material on cardiovascular system in experimental rats when administered intraduodenally. Formulation when administered to normotensive, anaesthetized, male Wistar rats intraduodenally with three different doses (50, 100 & 200 mg/kg) showed no effect (increase or decrease) on blood pressure, heart rate & respiration. The observations were taken up to three hours at one hour interval after the drug administration. In all the three parameters at graded doses no change has been observed at any interval of the time.

The results are tabulated as Tables 9-11

TABLE 9

Effect of test drug on blood pressure in anaesthetized male rats

| | Blood Pressure (mmHg) | | | |
|---|---|---|---|---|
| Dose | Initial | 1 hour | 2 hour | 3 hour |
| Formulation 50 mg/kg | 186.66 ± 1.69 | 186.66 ± 4.70 | 182.00 ± 4.96 | 183.66 ± 2.62 |
| Formulation 100 mg/kg | 190.66 ± 4.10 | 198.33 ± 10.27 | 192.00 ± 9.21 | 191.66 ± 13.12 |
| Formulation 200 mg/kg | 184.66 ± 3.68 | 190.33 ± 2.35 | 186.66 ± 4.71 | 185.00 ± 0.00 |

The data showed no significant increase/decrease on blood pressure in treated animals.

TABLE 10

Effect of test drug on respiration in anaesthetized male rats

| | Respiration rate (breaths/min.) | | | | |
|---|---|---|---|---|---|
| Dose | Initial | 30 min | 1 hour | 2 hour | 3 hour |
| Formulation 50 mg/kg | 89.02 ± 1.55 | 87.66 ± 2.05 | 90.33 ± 2.05 | 91.83 ± 3.74 | 89.66 ± 2.18 |
| Formulation 100 mg/kg | 92.33 ± 5.43 | 91.45 ± 4.21 | 92.84 ± 2.35 | 88.76 ± 2.81 | 90.23 ± 3.57 |
| Formulation 200 mg/kg | 90.33 ± 2.05 | 89.66 ± 5.79 | 92.00 ± 4.32 | 92.33 ± 5.43 | 93.00 ± 6.68 |

The data showed no significant increase/decrease on respiration rate in treated animals

TABLE 11

Effect of test drug on Heart rate in anaesthetized male rats

| | Heart rate (beats/min.) | | | |
|---|---|---|---|---|
| Dose | Initial | 1 hour | 2 hour | 3 hour |
| Formulation 50 mg/kg | 328.33 ± 5.88 | 325.00 ± 7.07 | 331.25 ± 11.57 | 329.14 ± 6.40 |
| Formulation 100 mg/kg | 333.33 ± 6.23 | 336.66 ± 4.71 | 328.64 ± 11.11 | 331.31 ± 9.65 |

TABLE 11-continued

| Effect of test drug on Heart rate in anaesthetized male rats | | | | |
|---|---|---|---|---|
| | Heart rate (beats/min.) | | | |
| Dose | Initial | 1 hour | 2 hour | 3 hour |
| Formulation 200 mg/kg | 321.66 ± 13.12 | 328.33 ± 12.47 | 318.33 ± 8.49 | 313.33 ± 4.71 |

The data showed no significant increase/decrease on heart rate in treated animals The results indicated that the formulation is very safe and exhibited an excellent aphrodisiac potential useful for the management of male sexual dysfunction.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A method for treating male sexual dysfunction in mammals comprising administering to a subject in need thereof an effective dose of a composition, wherein the composition comprises:

60-65% w/w *Withania somnifera* extract standardized to contain 0.25% withaferin and 7% withanolides, 12-18% w/w *Mucana pruriens* extract standardized to contain 10% w/w L-dopa, 5-10% w/w *Coleus forskolii* extract standardized to contain 10% w/w forskolin, 12-18% w/w *Kaempferia parviflora* standardized to contain 2.5% w/w of 5,7-dimethoxyflavone and not less than 10% w/w Total flavanoids and 0.1-2% w/w *Piper nigrum* extract standardized to contain 95% w/w piperine;

wherein the male sexual dysfunction is selected from the group consisting of: erectile dysfunction, premature ejaculation, delayed or inhibited ejaculation, and reduced libido.

2. The method as in claim 1, wherein the male sexual dysfunction is erectile dysfunction and reduced libido.

3. The method as in claim 1, wherein the management of male sexual dysfunction is brought about by inhibiting phospho diesterase 5 (PDE-5), enhancing testosterone, Nitric oxide and cGMP levels and activating androgen receptor and cGMP protein kinase.

4. The method as in claim 1, wherein the effective dose of the composition is 50-200 mg/kg body weight.

5. The method as in claim 1, wherein the mammal is male.

6. The method as in claim 1, wherein the mammal is human.

7. The method as in claim 1, wherein the composition is formulated with pharmaceutically/nutraceutically acceptable excipients, adjuvants, diluents or carriers and administered in the form of tablets, capsules, syrups, gummies, powders, suspensions, emulsions, chewables, candies or eatables.

* * * * *